US00PP13120P2

(12) United States Plant Patent
Carruth

(10) Patent No.: US PP13,120 P2
(45) Date of Patent: Oct. 22, 2002

(54) HYBRID TEA ROSE PLANT NAMED 'WEKQUANEZE'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/715,650

(22) Filed: Nov. 17, 2000

(51) Int. Cl.[7] ..... A01H 5/00
(52) U.S. Cl. ..... Plt./137
(58) Field of Search ..... Plt./137

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Hybrid Tea rose suitable for garden decoration, having flowers of blended red-purple coloration.

1 Drawing Sheet

BACKGROUND OF THE INVENTION

This invention relates to a new and distinct variety of Hybrid Tea. The varietal denomination of the new variety is *Rosa hybrida* cv. 'WEKquaneze'. It has an undistributed seedling of my creation as its seed parent and as its pollen parent the variety known as 'MACgenev' (U.S. Plant Pat. No. 8,279).

SUMMARY OF THE INVENTION

Among the features which distinguish the new variety from other presently available and commercial rose cultivars known to the inventor are the following combination of characteristics: its blend of many red-purple colorations, it strongly fragrant flowers and its darkly tinted foliage. The plant has an upright bushy growing habit, suitable for outdoor garden decoration.

Asexual reproduction of the new variety by budding as performed in Kern County and Upland, Calif., shows that the foregoing and other distinguishing characteristics come true to form and are established and transmitted through succeeding propagations. 'WEKquaneze' may be asexually propagated by cuttings, budding and grafting.

COMPARISON WITH PARENTS

The new variety may be distinguished from its pollen parent, an undisseminated seedling of my creation, by the following combination of characteristics: whereas 'WEKquaneze' bears flowers of blended red-purple coloration, the seed parent bears flowers of significantly lighter lavender coloration. The new variety bears dark green glossy foliage often suffused with dark pigmentation, whereas the seed parent bears lighter green matte foliage with significantly less dark pigmentation.

The new variety may be distinguished from its pollen parent, 'MACgenev', by the following combination of characteristics: whereas 'WEKquaneze' bears flowers of blended red-purple coloration, 'MACgenev' bears flowers of blended lighter pink tones. The pollen parent bears flowers with about 34 to 39 petals, whereas the new seedling bears flowers of lighter petalage (about 25 to about 31).

BRIEF DESCRIPTION OF ILLUSTRATION

The accompanying photograph illustrates specimens of the new variety and shows the flowering thereof from bud to full bloom depicted in color as nearly correct as it is possible to make in a color illustration of the character. Throughout this specification, color values are based upon The Colour Chart of The Royal Horticultural Society of London, England, (1995 ed.) except where common terms of color definition are employed.

DESCRIPTION OF THE NEW VARIETY

The following description is of 3 to 4 year old rose plants of the new cultivar grown outdoors in Upland, Calif. in the month of October. Phenotypic expression may vary with environmental, cultural and climatic conditions, as well as differences in conditions of light and soil.

FLOWER

The new variety sometimes bears its flowers singly, sometimes in clusters of three to four or more flowers per stem. Flowers are borne in somewhat irregular to rounded clusters on strong medium length stems (about 23 to about 36 cms.). Outdoors, the plant blooms abundantly and nearly continuously during the growing season. The flowers have a very strong rose and citrus blossom fragrance.

BUD

The peduncle is about 3.7 to about 6.0 cms. in length. It is moderately smooth with some stipitate glands. Peduncle color is between 144A and 138B often heavily suffused especially on the side exposed to the sun with between 183B and 187B.

Before the calyx breaks, the bud is about 1.4 to about 1.9 cms. in diameter at the widest point, about 2.1 to about 2.8 cms. in length, and pointed to ovoid in shape. The surface of the bud bears few slender foliaceous appendages and some stipitate glands, usually with stout moderately cut foliaceous parts extending beyond the tip of the bud about ½ or more of its length. Bud color is between 139C and 144A often heavily suffused with between 183B and 187B.

The inner surface of the sepals is covered with fine wooly tomentum; sepal margins are lined with many stipitate glands and hairs.

As the petals open (after the calyx breaks), the bud is about 1.9 to about 2.7 cms. in diameter at the widest point, about 2.6 to about 3.5 cms. in length, and very pointed to ovoid in form. The color of the under surfaces of the newly opened petals is between 60A and 59A. At the point where the petal attaches, there is a moderately small zone of between 1C and 2C. The color of the upper surfaces of the newly opened petals is between 71A and 70A. At the point where the petal attaches, there is a slightly larger zone of between 1C and 2C.

BLOOM

When fully open, the bloom ranges from about 9.2 to about 12.3 cms. in diameter. Petalage is double with about 25 to 31 petals and about 3 to 6 petaloids arranged irregularly. When partially open, the bloom form is somewhat high centered to cupped, and the petals are moderately spiraled to cupped with petal edges somewhat reflexed outward. The petal margin is entire. Petals are about 3.4 to about 4.8 cms. in length and about 2.7 to about 4.9 cms. in width at the widest point. When fully open, the bloom form is more cupped, and the petals are more cupped to slightly undulated with petal edges somewhat reflexed outward.

PETALS

The substance of the petals is moderately heavy to leathery and of medium thickness with upper surfaces somewhat satiny and under surfaces slightly shiny to somewhat matte. The outer petals are nearly round to very broadly obovate in shape with rounded apices. The inner petals are more broadly obovate in shape with rounded apices.

NEWLY OPENED FLOWER

The under surface of the outer petals is blended with as dark as between 60A and 59B to as light as between 61B and 60C. At the point where the petal attaches, there is a moderately small zone between 1D and 2C. The upper surface of the outer petals is between 70C and 73B often heavily blushed near the petal edge with between 60A and 59C. At the point where the petal attaches there is a slightly larger zone between 1D and 2C.

The under surface of the intermediate and inner petals are blended with as dark as between 61B and 67A to as light as between 68B and 73B. The upper surface of the intermediate and inner petals is between 70C and 73C sometimes blushed near the petal edge with between 59C and 60A.

The general tonality of the newly opened flower is between 70C and 73B often blushed on the outermost petal edges with between 59C and 60A.

THREE-DAY-OLD FLOWER

The under surface of the outer petals is blended with as dark as between 60B and 64A to as light as between 61C and 60D. At the point where the petal attaches, there is a moderately small zone between 2D and 4C. The upper surface of the outer petals is between 73B and 70C often heavily blushed near the petal edge with between 60B and 64A. At the point where the petal attaches there is a slightly larger zone between 4D and 2D.

The under surface of the inner petals is blended with as dark as between 73A and 70B to as light as between 75B and 73C. The upper surface of the inner petals is between 75B and 73C with no blush coloration.

The general tonality of the three-day-old flower is between 73B and 75B often blushed on the outermost petal edges with between 60B and 64A.

On the spent bloom, the petals usually drop off cleanly. In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are numerous (average about 165) and are arranged regularly about the pistils; a few are mixed with petaloids. The filaments are irregular in length most with anthers. Filaments are between 8C and 9D in color sometimes blushed near the top with near 64C. The anthers open approximately at the same time. Anther color is between 18A and 22B when immature and between 164B and 165C at maturity. Pollen is moderately abundant and near 8D in color. The filaments are about 0.6 to about 0.9 cm in length. The anthers are about 0.2 to about 0.4 cm in length. The styles are about 0.5 to about 0.8 cm. in length.

FEMALE REPRODUCTIVE ORGANS

Pistils vary in number (average about 125) . The styles are somewhat thin moderately bunched to somewhat separated. Stigma color is near 8C. Style color is between 8B and 8C. Ovaries are usually all enclosed in the calyx.

Hips are somewhat short in length, very globular in form, and near 24A in color when ripe. The hip surface is moderately smooth with thick fleshy walls. The sepals are fugacious. There are approximately 3 to 8 seeds, moderately small in size.

FOLIAGE

The compound leaves are usually comprised of three to five or more leaflets and are borne abundantly. The five-leaflet leaves are about 10.5 to about 12.5 cms. in length and about 9.2 to about 12.0 cms. in width at the widest point, moderately leathery in texture and glossy in finish. The terminal leaflets are about 5.8 to about 7.4 cms. in length and about 3.7 to about 4.9 cms. in width at the widest point, shaped somewhat oval to ovate with somewhat acute apices and moderately rounded bases. Their margins are usually simply serrate. The venation pattern of the leaf is pinnate and the vein color is between 138B and 147B.

The upper surface of the mature leaf is between 137A and 139A. The under surface of the mature leaf is between 138B and 138C often moderately suffused with between 183B and 187C. The upper surface of the young leaf is between 143B and 144A, often heavily suffused with between 183B and 187A. The under surface of the young leaf is between 144A and 138B, often heavily suffused with between 183B and 187B.

The rachis is somewhat heavy in caliper and moderately rough. The upper side is shallowly grooved with some hairs and stipitate glands on the edges of the grooves. The under side of the rachis is somewhat rough with many hairs, some stipitate glands and few very small prickles.

The stipules are about 1.4 to about 1.8 cms. in length and of medium width and with straight points that usually turn out at an angle of less than 45 degrees.

The sepals are about 5 in number, about 2.3 to about 3.1 cms. in length and 0.9 to about 1.2 cms. in width at the widest point. The color of the sepals are the same as the color of the mature foliage.

The plant displays an average degree of resistance to powdery mildew and rust as compared to other commercial varieties grown under comparable conditions in Upland, Calif.

GROWTH

The plant has an upright medium growth habit (about 125 to about 160 cms. in height and about 80 to about 115 cms. spread at the widest point), with moderately full branching. It displays moderately vigorous growth. As indicated by the USDA Plant Hardiness Zone Mao, the plant's winter hardiness is between zones 5b and 6a. The plant's drought/heat tolerance is yet to be determined.

The color of the major stems is between 138A and 146B. They bear many large prickles that are about 0.7 to about 1.2 cms. in length. The large prickles are almost straight angled slightly downward with a moderately broad oval base; prickle color is between 165A and 174A. The major stem bears few small prickles. The diameter of the stem is about 1.8 to about 3.2 cms. at the widest point.

The color of the branches is between 137C and 146A. They bear some large prickles which are of similar size and shape to the large prickles on the major stems; prickle color is between 163C and 164C. The branches bear some small prickles of similar shape and coloration.

The color of the new shoots is near 144A usually heavily suffused especially on the side exposed to the sun with between 183B and 187B. They bear some prickles of various sizes but of similar shape to the prickles on the major branches; prickle color is between 183B and 187B.

I claim:

1. A new and distinct Hybrid Tea rose plant of the variety substantially as described and illustrated herein.

* * * * *

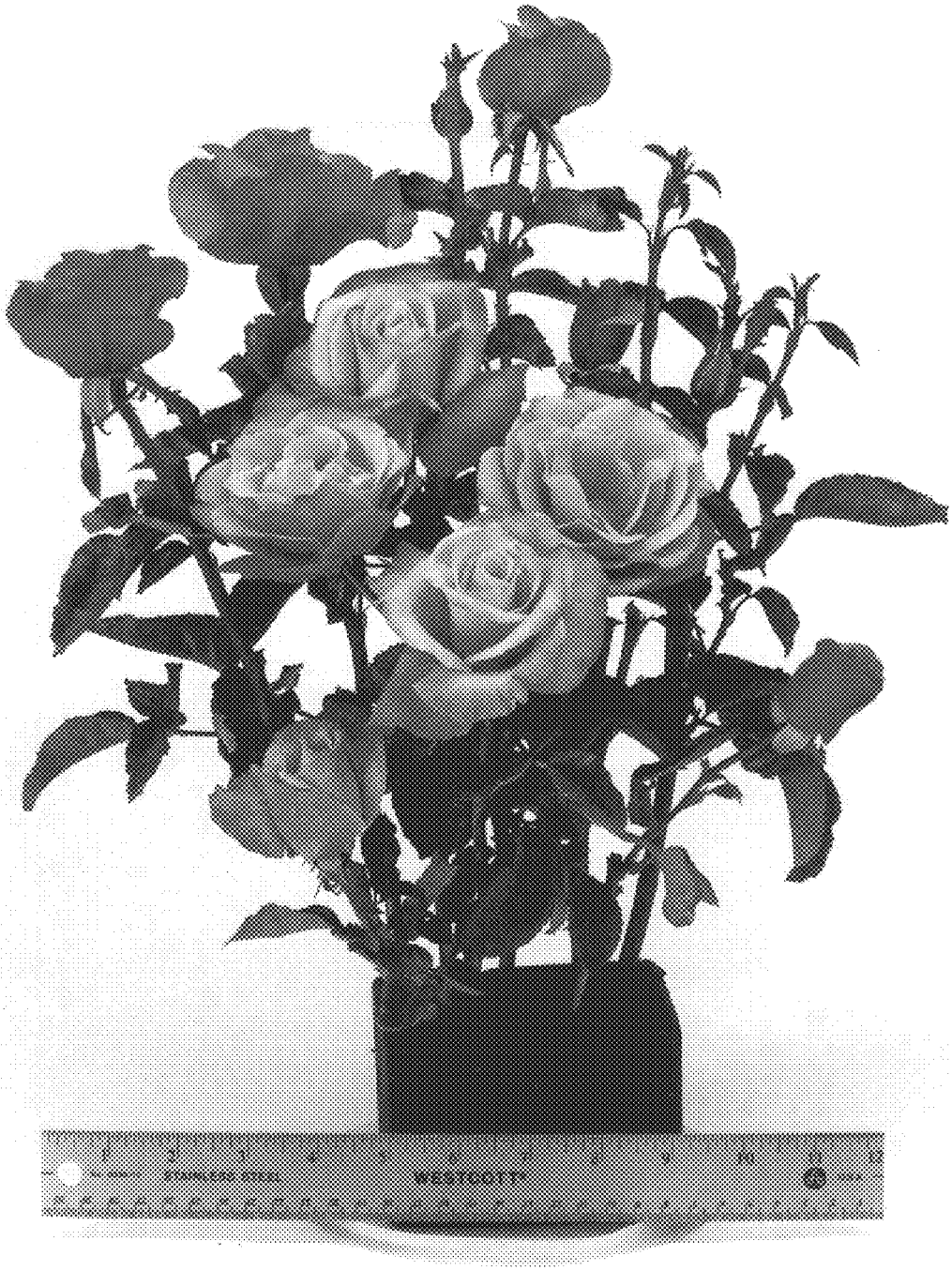
WESTCOTT